United States Patent
Allsworth

(10) Patent No.: US 8,334,782 B2
(45) Date of Patent: Dec. 18, 2012

(54) SMOKE DETECTOR AND IONISATION APPARATUS

(75) Inventor: Max D. Allsworth, Islington (GB)

(73) Assignee: Walter Kidde Portable Equipment, Inc., Mebane, NC (US)

( * ) Notice: Subject to any disclaimer, the term of this patent is extended or adjusted under 35 U.S.C. 154(b) by 746 days.

(21) Appl. No.: 12/373,298

(22) PCT Filed: Jul. 11, 2007

(86) PCT No.: PCT/GB2007/002587
§ 371 (c)(1),
(2), (4) Date: Sep. 18, 2009

(87) PCT Pub. No.: WO2008/007084
PCT Pub. Date: Jan. 17, 2008

(65) Prior Publication Data
US 2010/0032560 A1    Feb. 11, 2010

(30) Foreign Application Priority Data

Jul. 12, 2006  (GB) .................................. 0613882.0

(51) Int. Cl.
*G08B 17/10* (2006.01)
(52) U.S. Cl. ........ 340/629; 340/628; 340/577; 340/578; 340/579; 250/289; 250/389
(58) Field of Classification Search .................. 340/629, 340/628, 577, 578, 579; 250/289–389
See application file for complete search history.

(56) References Cited

U.S. PATENT DOCUMENTS 4,617,560 A * 10/1986 Gutmann ...................... 340/628

(Continued)

FOREIGN PATENT DOCUMENTS

EP    1397030 A1    3/2004

(Continued)

OTHER PUBLICATIONS

Database Inspec (Online); The Institution of Electrical engineers, Stevenage, GB; Dec. 24, 2004; Knapp W., et al., "Carbon Buckypaper field emission investigations" XP002454638, Database accession No. 7635888 cited in the application abstract.

(Continued)

*Primary Examiner* — Tai T Nguyen
(74) *Attorney, Agent, or Firm* — Carlson, Gaskey & Olds PC

(57) ABSTRACT

A smoke detector comprises a soft x-ray source (10) and an air space (16) communicating with ambient air (18) and positioned so that soft x-rays produced by the soft x-ray source (10) pass into the air space (16) to ionise air in the air space (16). A detector (14) is positioned for detecting ionised air in the air space (16). Smoke particles entering into the air space (16) mop up ionised air. This leads to a reduction in the number of ions detected which triggers an alarm. The soft x-ray source (10) preferably comprises a substrate (22) on which are provided a plurality of nanometer scale elongate structures (28). The elongate structures (28) are provided in an evacuated chamber (42) formed between the substrate (22), a spacer (30), and a laminated film (36). The laminated film (36) comprises an aluminum foil layer (38) and a supporting nylon layer (40). A voltage converting circuit (44) is powered by a 9 volt DC battery and applies a 1.5 kV DC voltage between the substrate (22) and the aluminum foil layer (38). In use, the electrical voltage induces field emission of electrons from the elongate structures (28). The electrons are accelerated across the chamber (42) to the aluminum foil layer (38), where they collide with the foil layer (38) and produce the soft x-rays.

30 Claims, 2 Drawing Sheets

U.S. PATENT DOCUMENTS

Figure 1:
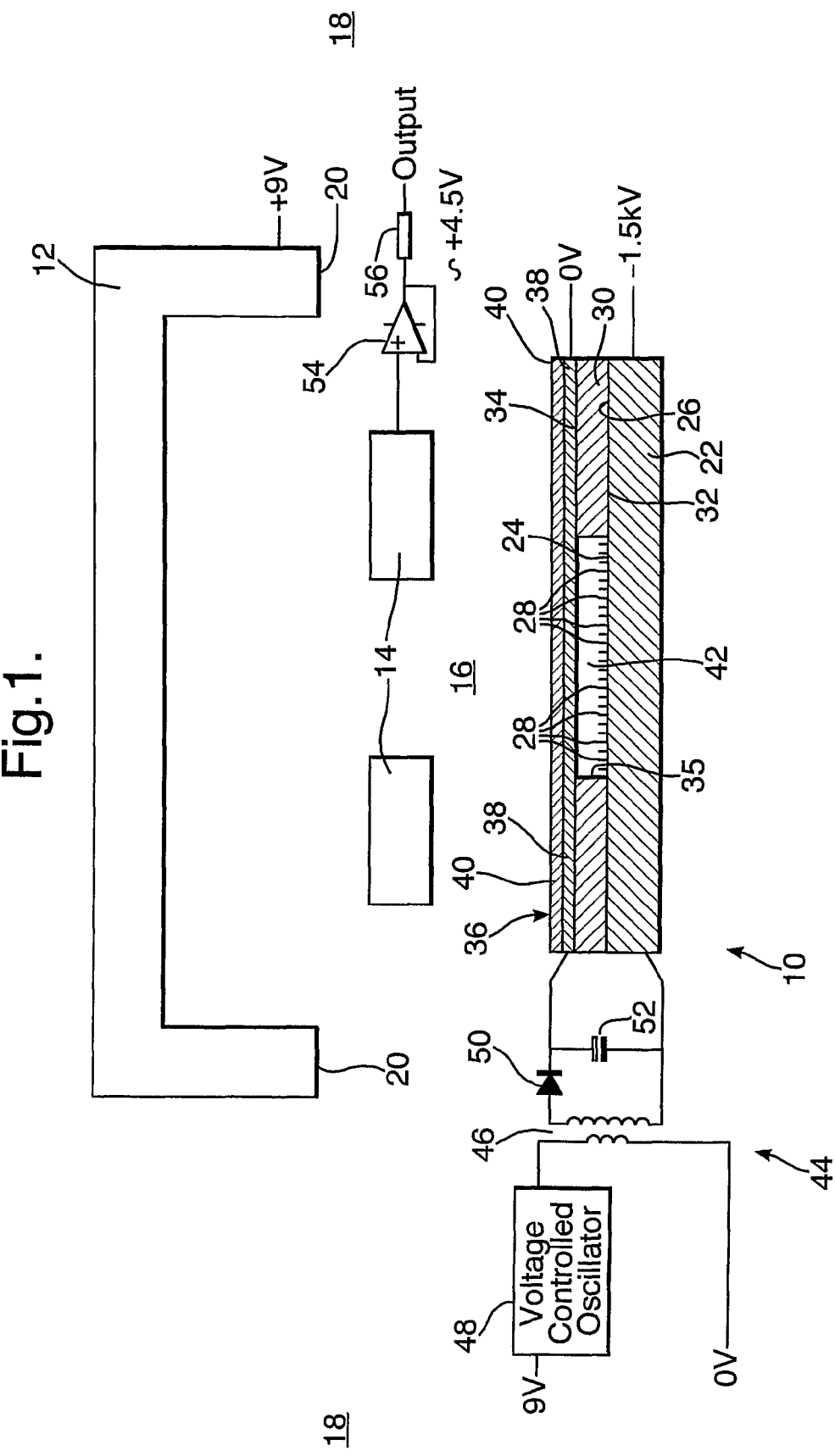

| | | | | |
|---|---|---|---|---|
| 4,786,811 A * | 11/1988 | Sasaki | 250/385.1 |
| 4,845,474 A * | 7/1989 | Moore et al. | 340/629 |
| 4,864,141 A * | 9/1989 | Lewiner | 250/381 |
| 5,243,330 A * | 9/1993 | Thuillard | 340/629 |
| 5,751,218 A * | 5/1998 | Winterble et al. | 340/693.6 |
| 6,429,426 B1 | 8/2002 | Doring | |
| 6,740,874 B2 | 5/2004 | Doring | |
| 7,196,631 B1 * | 3/2007 | Dziekan et al. | 340/628 |
| 7,809,112 B2 * | 10/2010 | Derra et al. | 378/122 |
| 2004/0108298 A1 | 6/2004 | Gao | |
| 2004/0150322 A1 | 8/2004 | Busta | |
| 2005/0127351 A1 | 6/2005 | Tolt | |

FOREIGN PATENT DOCUMENTS

| | | |
|---|---|---|
| WO | 9750160 | 12/1997 |
| WO | 0045354 | 8/2000 |
| WO | 2004081527 A3 | 9/2004 |

OTHER PUBLICATIONS

International Search Report and Written Opinion of the International Searching Authority for International application No. PCT/GB2007/002587 mailed Oct. 29, 2007.

* cited by examiner

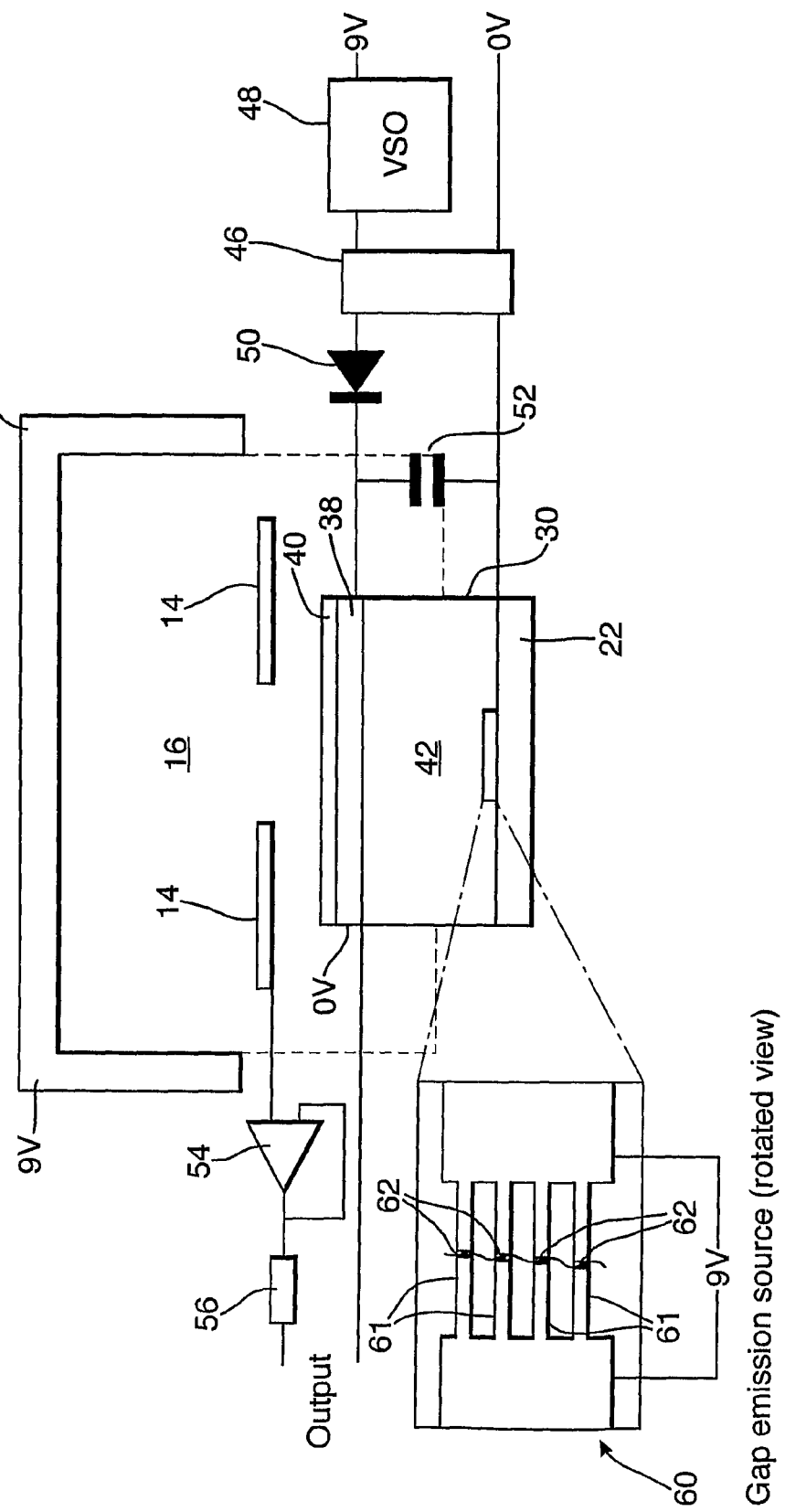

SMOKE DETECTOR AND IONISATION APPARATUS

The invention relates to a smoke detector and to a method of detecting smoke. The invention also relates to an ionisation apparatus.

A well known type of smoke detector makes use of Americium 241 as a source of alpha particles. The smoke detector includes an internal space which communicates with ambient air. The space is positioned adjacent the Americium 241 so that alpha particles emitted from the Americium 241 pass into the space and ionise air within the space. The space is defined by a metal cover which is maintained at a positive voltage (e.g. +9V). Air which has been ionised by the alpha particles is accelerated towards the cover, and a proportion of the ions collide with a collector electrode located between the alpha particle source and the cover. If smoke enters into the internal space the smoke interacts with the ions and increases the impedance of the air in the internal space. This can be detected in many ways—for example by measuring the voltage at the collector electrode.

Smoke detectors of this known type are relatively inexpensive, have a relatively long lifetime, and can be operated for long periods of time using a battery. However, proper disposal of the radioactive Americium 241 can be expensive and, for this reason, it is desirable to produce a smoke detector which does not use Americium 241 or similar radioactive elements.

According to a first aspect of the invention, there is provided a smoke detector comprising: a source of soft x-rays; a space communicating with ambient air and positioned so that soft x-rays produced by the soft x-ray source pass into the space to ionise air in the space; and a detector for detecting the presence of smoke in the space by detecting ionised air.

According to a second aspect of the invention, there is provided an ionisation apparatus comprising a soft x-ray source and a chamber positioned so that soft x-rays produced by the soft x-ray source pass into the chamber to ionise a fluid in the chamber; the soft x-ray source comprising: an electron source; circuitry for applying an electrical field to cause field emission of electrons from the electron source; and a target positioned for interaction with the electrons emitted from the electron source and for producing the soft x-rays in response thereto.

According to a third aspect of the invention, there is provided a method of detecting smoke comprising: producing soft x-rays, using the soft x-rays to ionise air, and detecting the ionised air.

For the present purposes the term soft x-ray means x-rays having a peak energy of 12.4 keV or less. In general the peak energy of the x-rays will be 10 keV or less.

The following is a more detailed description of embodiments of the invention, by way of example, reference being made to the appended drawings in which:

FIG. 1 is a schematic representation, partially in cross-section, of a first embodiment of the invention; and FIG. 2 is a schematic representation, partially in cross-section, of an alternative embodiment of the invention.

As seen in FIG. 1, a smoke detector comprises a source 10 of soft x-rays, a cover 12 and a collector electrode 14. An air space 16 is located between the soft x-ray source 10 and the cover 12 and the collector electrode 14 is located within the air space 16 between the soft x-ray source 10 and the cover 12. The air space 16 is connected to ambient air 18 via openings 20.

The soft x-ray source 10 comprises a substrate 22 which is formed from an electrically conductive material. The substrate 22 has a surface having a central portion 24 surrounded by a peripheral portion 26. Very many thousands or millions of nanometer scale elongate structures 28 extend from the central portion 24 of the surface in a direction generally away from the substrate 22.

The nanometer scale elongate structures 28 may be, for example, carbon nanotubes (single walled or multiwalled), zinc oxide nanorods, silicon nanorods, boron nitride nanorods, or titanium dioxide nanorods. They may be any suitable elongate structure having dimensions on the nanometer scale. The elongate structures 28 (or at least some of them) should be electrically conductive under the conditions used in operation. In this regard, zinc oxide is a semiconductor but is in a conductive state due to the electric field applied in operation. Carbon nanotubes exist in two molecular forms—one of which is conductive and the other one is non-conductive. The conductive and non-conductive forms occur in a 50:50 mixture with field emission being less effective (than might be expected from the nanotube density alone) as only half of the carbon nanotubes conduct.

The nanometer scale elongate structures 28 preferably have a width of no more than about 200 nanometers. More preferably, the width is no more than about 100 nanometers. Ideally, the width is about ten nanometers or less. The most preferred elongate structures 28 have a width of between 0.4 nanometers and 10 nanometers and a length of between 100 nanometers and 100 micrometers.

In many cases, the nanometer scale elongate structures 28 will have been grown on the central portion 24 of the surface of the substrate 22.

For the purposes of the present example, the elongate structures 28 take the form of carbon nanotubes grown on an electrically conductive substrate, the nanotubes combined with the substrate being commercially available from Xintek Inc. (North Carolina, USA) under the product description electron field emission diode cathode. The substrate of the commercially available product may be used as the substrate 22 or it may be mounted on a supporting structure so that the product substrate together with the supporting structure form the substrate 22 of the smoke detector.

A spacer 30, formed from a non-electrically conductive material, has first and second opposed surfaces 32, 34 and a central opening 35 which extends between the first and second surfaces 32, 34. The first surface 32 of the spacer 30 is attached, in an air-tight manner, to the peripheral portion 26 of the surface of the substrate 22, so that the nanoscale elongate structures 28 lie within the central opening 35 of the spacer 30. The spacer 30 preferably has a thickness in the range of from about 0.2 mm to about 10 mm. For example, it may have a thickness of about 3 mm. The spacer 22 can be, for example, formed of silicon dioxide.

The soft x-ray source 10 also comprises a film 36 consisting of an aluminium foil layer 38 laminated to a supporting nylon layer 40. As shown in the figure, the aluminium foil layer 38 of the film 36 is bonded to the second surface 34 of the spacer 30. The aluminium foil layer 38 may be bonded to the spacer 30 by, for example, anodic bonding under vacuum conditions.

The aluminium foil layer 38 preferably has a thickness in the range of about 80 nanometers to about 1000 nanometers, more preferably in the range of about 80 nanometers to about 240 nanometers. The thickness of the nylon supporting layer 40 should be sufficient to provide adequate structural support to the aluminium foil layer 38.

Accordingly, as shown in the figure, the spacer opening 35 is closed on one side, in an air-tight manner, by the substrate 22, and on the other side, in an air tight manner, by the film 36 so as to form an enclosed chamber 42. The chamber 42 is evacuated to the order of about 10 Torr or less. The nanoscale elongate structures 28 lie within the evacuated chamber 42 and are spaced from the aluminium foil layer 38 by about the thickness of the spacer 30.

The soft x-ray source 10 also includes a voltage converting circuit 44 which uses a transformer 46 to convert an input voltage of 9 volts to an output voltage in the range of about 1.5 kV to about 4.5 kV, preferably about 3 kV. On the input side of the transformer 46, a voltage controlled oscillator 48 converts a 9 volt DC current from a battery to a 9 volt AC current which forms the input to the transformer 46. At the output side of the transformer 46, a first output line is connected to the aluminium foil layer 38 via a diode 50 and a second output line is connected to the substrate 22. The diode 50 serves to rectify the output from the transformer 46. A reservoir capacitor 52 is connected between the first and second output lines and serves to smooth the output voltage. As shown in the figure, the voltage converting circuit 44 applies a voltage in the range of about −1.5 kV to −4.5 kV (preferably about −3 kV) to the substrate 22, as compared to the aluminium foil layer 38 (0V).

The collector electrode 14 is connected in series first to an amplifier 54 and then to a resistor 56.

The cover 12 is made of a metal and is held at +9V, relative to the aluminium foil 38 (0V) using the same 9V DC battery which is used to power the voltage converting circuit 44.

The operation of the smoke detector will now be described.

The relatively large voltage applied between the substrate 22 and the aluminium foil layer 38 causes field emission of electrons (also known as Fowler-Nordheim Tunnelling) from the nanometer scale elongate structures 28 into the vacuum in the chamber 42. Heating to relatively high temperatures is normally required in order to obtain field emission. However, the nanometer scale elongate structures 28 act as very sharp points and the electric field becomes concentrated at the tips of the elongate structures 28. In turn, this results in field emission occurring at room temperature, which is clearly advantageous in terms of the lifetime and power consumption of the smoke detector.

The electrons emitted from the nanometer scale elongate structures 28 into the evacuated chamber 42 are accelerated towards the aluminium foil layer 38 by the voltage applied between the foil layer 38 and the substrate 22. When the electrons collide with the aluminium foil layer 38, soft x-rays are produced. The aluminium foil layer 38 is sufficiently thin so that the x-rays can pass across the aluminium foil layer 38, and through the nylon supporting layer 40 into the air space 16. The nylon supporting layer 40 has a very low absorption for x-rays.

The x-rays produced have a range of energies with a peak at about 1.5 keV from the K-alpha line and with lower energy x-rays produced by bremsstrahlung processes. X-rays of about 1.5 keV have a range in air of about 8 mm which corresponds generally to the distance between the aluminium foil layer 38 and the cover 12.

X-rays emitted into the air space 16 interact with the air to form ions. Ions formed in this way are accelerated towards the cover 12 by virtue of the positive voltage (+9V) applied to the cover 12 relative to the aluminium foil layer 38 (0V).

The collector electrode 14 sits at a potential half way between the cover 12 and electrode 38, which is approximately 4.5V in the absence of smoke because of the relative impedances of the air between the three electrodes (that is to say the cover 12, the collector electrode 14, and the aluminium foil 38). This voltage is output via high impedance amplifier 54. The output signals may be fed to a microprocessor via an analogue to digital converter, or to an alarm relay.

As described above, the air space 16 is open to ambient air 18 via the openings 20 and so in the presence of smoke, smoke particles enter through the openings 20 into the air space 16. Smoke particles interact with the ions in the air space 16 and this, in turn, reduces the number of ions colliding with the collector electrode 14 and the number of ions colliding with the cover 12. The geometry of the system is such that smoke diffuses first into the region of the air space 16 adjacent the cover 12 and so, in the presence of smoke, the voltage at the collector electrode 14 falls as the impedance of the air between the cover 12 and electrode 14 increases. The change in the voltage is detected and is used to trigger an alarm. This detection of a change in voltage is used in known smoke detectors (which use an alpha emitter rather than a source of soft x-rays in order to ionise air).

Aluminium is a preferred metal for the foil layer 38 because aluminium is a relatively effective metal for producing x-rays and because aluminium is also cheap and non-toxic. However, other metals can be used for the production of x-rays. Another potential metal is beryllium which is also an effective metal for producing x-rays. However, beryllium is not as desirable as aluminium as it is more expensive and has toxicity issues.

The thickness of the metal foil layer 38 is preferably chosen so as to maximise x-ray emission into the air space 16. In order to maximise x-ray production, the metal foil layer 38 should have a thickness at least equal to the penetration depth of the electrons in the metal. The penetration depth depends on the metal chosen and also on the energy of the electrons. However, absorption of x-rays by the metal foil layer 38 also increases with increasing thickness of the metal foil layer 38. Accordingly, in order to maximise emission of x-rays into the air space 16, the metal foil layer 38 should be no thicker (and possibly even thinner) than the penetration depth of the electrons, because additional thickness of the metal foil layer 38 increases absorption of the x-rays by the metal foil layer 38. When, as in the embodiment described above, the metal foil layer 38 is made of aluminium, then the ideal thickness of the metal foil layer 38 may be in the range of from about 80 nanometers to about 240 nanometers. At these thicknesses, the nylon supporting layer 40 may be required in order to provide the mechanical strength to the film 36 so as to resist the forces applied by the pressure difference across the film 36.

Of course, the nylon supporting layer 40 may be omitted if the metal foil layer 38 is sufficiently strong in itself so as to resist the pressure difference across it. In this case, it may be necessary for the metal foil layer 38 to have a thickness greater than that required for optimum x-ray emission into the air space 16. If a supporting layer 40 is used, it need not be nylon and could be any suitable polymer.

The voltage applied between the metal foil layer 38 and the substrate 22 is chosen to give a relatively high degree of x-ray emission while maintaining a relatively low power consumption. The voltage is chosen dependent on the metal used for the metal foil layer 38—in accordance with the x-ray production and absorption properties of the metal. For example, when the metal foil layer 38 is aluminium, a voltage of 1.5 kV or greater is preferred. The voltage applied between the metal foil layer 38 and the substrate 22 influences the energy of the electrons accelerated towards the metal foil layer 38 according to the formula $E=Q*V$ (where E is energy, Q is charge and V is Volts). For aluminium, 1.47 keV is the minimum electron energy needed to get the right K shell transition for K-alpha line x-ray emission. As the electron energy increases from 1.47 keV up to about 4.5 keV, the K-alpha line X ray emission increases greatly. However, aluminium demonstrates an x-ray absorption peak for x-rays having an energy greater than 1.55 keV. Hence a good x-ray emission is obtained, when the metal foil layer 38 is aluminium, using an accelating voltage of between about 1.5 and about 4.5 kV, preferably about 3 kV.

As described above, the distance between the nanometer scale elongate structures 28 and the metal foil layer 38 corresponds generally to the thickness of the spacer 30. The distance between the nanometer scale elongate structures 28 and the metal foil layer 38 is important as this defines the electron current. Field emission depends on the number of volts per unit distance between the elongate structures 28 and the metal foil layer 38. The voltage will be generally chosen so as to determine the required electron energy, and therefore the required x-ray energy. The distance between the nanometer scale elongate structures 28 and the metal foil layer 38 may be chosen in order to maximise the number of volts per unit distance with a view to maximising electron field emission.

It will be appreciated that the cover 12 and the collector electrode 14 need not have the configurations shown in the figure. Any suitable configuration may be used. Further, the assembly comprising the substrate 22, the elongate structures 28, the spacer 30 and the film 36 need not have the configuration shown in the figure. Any suitable configuration may be used. Moreover, it will be appreciated that the voltage converting circuit 44 need not be as shown in the figure. Any circuit suitable for applying the required voltage may be used.

Any suitable circuitry may be used to detect ions colliding with the collector electrode 14. Further, any other arrangement for detecting smoke in the air space 16 by detecting ionised air may be used.

It will be appreciated that the smoke detector embodiment described above is relatively simple and cheap in construction, utilises no expensive, toxic or radioactive components, and can be operated conveniently using a single 9 volt DC battery.

The smoke detector described above may be modified in a number of ways.

In a first modification, the elongate structures 28 and the substrate 22 take the form of zinc oxide nanoneedles grown on a substrate generally in accordance with the methods described by Tian, Z. R., et al. in *Nat. Mater.* 2 (2003) 821-826 and by Sounart, T. L., et al. in *Adv. Funct. Mater.*, 16 (2006) 335-344. Particularly suitable nanoneedle "forests" were obtained using the following experimental conditions.

A nanoparticle seeding solution was prepared as follows. One g ZnO nanoparticles (commercially available from Alfa Aesar; 24-71 nm by the manufacturer's specification) was dispersed in 10 g deionized $H_2O$. Sokolan CP10 (0.0388 g; BASF), a modified polyacrylic-based dispersant, was added. This suspension was stirred, sonicated and then centrifuged for 5 min at 3000 r.p.m. (IEC Central CL2 centrifuge/236 Aerocarrier rotor) to remove coarse agglomerates. Precleaned glass slides (25.4 mm×76.2 mm×1 mm, Fisher) were soaked in 70/30 $H_2SO_4/H_2O_2$ for 15 min, rinsed with deionized $H_2O$, dried with $N_2$ and subjected to 20 min $UV/O_3$ treatment (UVO-Cleaner, Jelight). When indium tin-oxide (ITO) coated glass slides were employed, these were cleaned by sonicating for 10 min. each successively in acetone, $CH_2Cl_2$, and methanol. When metal substrates were used (Ni, Co, Fe, W, Zn, Al, Stainless steel), these were polished to mirror finish (50 nm alumina particles utilized in the final polishing step), sonicated for 2 min. in $CH_2Cl_2$ to remove residual grease and cleaned under $UV/O_3$ producing lamp for 20 min. In the case of glass and ITO slides, the nanoparticle seeding solution (50 µl) was then spread over the clean substrate, allowed to dry in ambient, and further dried in an oven at 60° C. for 30 min. This seeding step was repeated one additional time to ensure complete substrate coverage with ZnO seeds. In the case of metal substrates, no seeding was performed. Following surface preparation, the substrates were then placed vertically in sealed 125 ml Teflon bottle containing 75 ml aqueous solution of 20 mM $Zn(NO_3)_2 \cdot 6H_2O$ (Fisher), 20 mM hexamethyltetramine (HMT, Fisher), and 125 mM diaminopropane (DAP, Aldrich). The reaction was performed for 24 hours at 60° C. yielding needle-like crystals preferentially oriented perpendicular to the substrate plane. The diameter of the needles produced in this way is 40-500 nm and their length is 2-3 µm (judged from the cross-section). The tip radius is 15-80 nm with a mean of 40 nm and standard deviation of 5 nm based on measurement of ~300 needles from 4 different samples.

In a second modification, the elongate structures 28 and the substrate 22 take the form of highly orientated zinc oxide nanoneedles grown on a substrate by a two stage process described below.

In the first stage, ~10 nm thick nanorods were grown on a clean glass substrate according to the method described by Greene, L. E., et al. in *Nano Lett.* 5 (2005) 1231-1236. Specifically, a five mM solution of zinc acetate dihydrate (99.999%, Aldrich) in ethanol (Fisher) was made by stirring at 60° C. for 1 hour. This solution (70 µl) was spread over the entire substrate, and was allowed to evaporate for 25 s before rinsing with a copious amount of ethanol. The zinc acetate coating procedure was repeated four additional times, and the substrate was placed in a box furnace (Lindberg) at 350° C. for 20 min to anneal the seeds. The entire seeding step was repeated one additional time. Seeded substrate was then placed vertically in sealed 125 ml Teflon bottle containing 75 ml aqueous solution of 25 mM $Zn(NO_3)_2 \cdot 6H_2O$ and 25 mM HMT. Following 120 min reaction at 92.5° C., the nanorod modified substrate was rinsed with deionized $H_2O$ and dried in air.

In the second stage, the nanorod modified substrates prepared in the first stage were reacted for 24 h at 60° C. in the-presence of 20 mM $Zn(NO_3)_2 \cdot 6H_2O$, 20 mM HMT, and 125 mM DAP to yield highly-oriented zinc oxide nanoneedle crystals. The diameter of the needles produced in this way is 30-400 nm, their length is 2-4 µm, and the tip radius is 21.4±3 nm (based on ~300 needles from 5 different samples).

In a third modification, the elongate structures 28 and the substrate 22 take the form of zinc oxide nanorods 28 grown on a zinc substrate 22 by the method described by Dev et al in Nanotechnology, 17 (2006), pp 1533 to 1540.

In a fourth modification, the elongate structures 28 take the form of carbon nanotubes 28 grown on a silicon or nickel substrate 22 by the method described by Y. B. Zhang et al. in App. Phys Lett. 86, 12 3115 (2005) or by the method described by M. Chhowalla et al. in App. Phys. Lett. 79, 13 2079 (2001).

Where elongate structures 28 such as nanoneedles or nanotubes are used in a "forest" (ie each structure 28 extending generally away from the substrate 22) to facilitate field emission of electrons, then thousands or millions of the elongate structures are preferably provided on the substrate 22. However, it is possible to use less and the number may be in the hundreds.

In a fifth modification, a sheet of carbon buckypaper may be used in place of the elongate structures 28 described above to achieve field emission of electrons. Carbon buckypaper is a non-woven mat formed from carbon nanotubes. Carbon buckypaper can be manufactured by, for example, the method of Y. A. Kim, et al. which is described in the article entitled "Fabrication of High-Purity, Double-Walled Carbon Nanotube Buckypaper", in Chemical Vapor Deposition, Volume 12, Issue 6, Pages 327-330, or by the method of Ji, Yunguang Lin, et al. which is described in the article entitled "Buckypaper's Fabrication and Application to Passive Vibration Control", in Nano/Micro Engineered and Molecular Systems, 2006. NEMS '06. 1st IEEE International Conference on, Publication Date: January 2006, pages 725-729. Electron field emission from carbon buckypaper has been described by Knapp, W., et al. in an article entitled "Field-emission characteristics of carbon buckypaper", in J. Vac. Sci. Technol. B 21(1), (2003), 557-561 and also by the same authors in an article entitled "Carbon Buckypaper field emission investigations", in Vacuum 69, (2003), 333-338.

When using carbon buckypaper in place of the elongate structures 28 described above, the buckypaper may be attached to the central portion 24 of the surface of the substrate 22 so that the buckypaper lies generally parallel to the surface of the substrate 24 in the evacuated chamber 42. Field emission of electrons may then take place predominantly from stray nanotubes projecting from the buckypaper into the evacuated chamber 42. Alternatively, a strip or strips of carbon buckypaper may be mounted on the central portion 24 of the surface of the substrate 22 generally perpendicularly to the central portion 24. In this case field emission of electrons may take place predominantly from ends of the nanotubes at the cut edges of the strips.

A sixth modification is shown in FIG. 2. In FIG. 2, components which are the same as the corresponding components in FIG. 1 are given the same reference numerals and are not discussed in detail. In the sixth modification, the elongate structures 28 are replaced by an array 60 of electron emitting elements 61 such as those described in EP 0788130, EP1324367, JP2000251641 or KR20020057637. These elements 61 utilise a small fissure 62 from which electrons are emitted on application of an electric field. The fissure generally has a width of less than 10 µm. The array 60 of the electron emitting elements is mounted on the substrate 22 and spaced from the aluminium foil layer 38 by the spacer 30. As for the embodiments which use elongate structures 28, electrons emitted from the electron emitting elements 61 are accelerated through the evacuated chamber 42 towards the aluminium target 38 where they generate soft x-rays. The subsequent operation is identical to the previous embodiments.

It will be appreciated that the smoke detectors described above include a soft x-ray source and a fluid ionisation apparatus which may be used in applications other than smoke detection. The fluid ionisation apparatus will generally have a chamber positioned so that soft x-rays produced by the soft x-ray source pass into the chamber to ionise a fluid in the chamber. Preferably, the chamber will be in fluid communication with a source of the fluid to be ionised. Means may be provided to control passage of the fluid into the chamber.

In the smoke detector example described above, the peak x-ray energy is about 1.5 keV. However, the x-rays generated can have different peak energies. For smoke detectors the peak x-ray energy will generally be less than 4 keV. 4 keV corresponds to a range in air of about 15 cm. For other applications, however, greater x-ray energies may be used.

The invention claimed is:

1. A smoke detector device, comprising:
   a chamber having a space configured to receive a fluid; and
   a source of soft x-rays positioned so that soft x-rays produced by the soft x-ray source pass into the space to ionise a fluid in the space; and
   a detector for detecting presence of smoke in the space by detecting ionised fluid.

2. The device of claim 1, wherein the soft x-ray source comprises:
   an electron source;
   circuitry for applying an electrical field to cause field emission of electrons from the electron source; and
   a target positioned for interaction with the electrons emitted from the electron source and for responsively producing the soft x-rays.

3. The device of claim 2, wherein the electron source comprises a plurality of points which are sufficiently sharp to facilitate electron field emission.

4. The device of claim 2, wherein the electron source comprises a plurality of nanometer scale elongate structures.

5. The device of claim 4, wherein the elongate structures have a width of no more than 200 nm.

6. The device of claim 5, wherein the elongate structures have a width of no more than 100 nm.

7. The device of claim 6, wherein the elongate structures have a width of no more than 10 nm.

8. The device of claim 4, wherein the elongate structures have a width of between 0.4 nm and 10 nm and a length of between 100 nm and 100 µm.

9. The device of claim 4, wherein each elongate structure has a tip, and an average diameter of the tips is less than 100 µm.

10. The device of claim 9, wherein the average diameter of the tips is less than 50 µm.

11. The device of claim 10, wherein the average diameter of the tips is less than 25 [µ]m.

12. The device of claim 4, wherein the elongate structures are selected from a group consisting of: carbon nanotubes; zinc oxide nanorods; silicon nanorods; boron nitride nanorods; and titanium dioxide nanorods.

13. The device of claim 2, wherein the electron source comprises an electrically conductive member having a generally planar surface and elongate structures attached to and extending away from the planar surface.

14. The device of claim 13, wherein the elongate structures extend generally perpendicularly to the planar surface.

15. The device of claim 13, wherein the elongate structures are provided by a sheet of carbon buckypaper.

16. The device of claim 2, wherein the electron source comprises an electron emitting element comprising an electron emitting fissure.

17. The device of claim 2, wherein the target comprises aluminum for producing the soft x-rays.

18. The device of claim 17, wherein the target comprises aluminum foil.

19. The device of claim 18, wherein the target comprises a supporting layer which has a lower x-ray absorption compared to aluminum.

20. The device of claim 18, wherein the aluminum foil has a thickness of between 80 nm and 1000 nm.

21. The device of claim 18, wherein the aluminum foil has a thickness of between 80 nm and 240 nm.

22. The device of claim 2, wherein the circuitry applies an electrical voltage of at least 1.5 kV between the electron source and the target to accelerate the electrons to the target.

23. The device of claim 22, wherein the electrical voltage is in a range from 1.5 kV to 4.5 kV.

24. The device of claim 2, wherein a distance from the electron source to the target is in the range of 0.2 mm to 10 mm.

25. The device of claim 2, wherein the target comprises a metal foil having a thickness which corresponds approximately to a penetration depth of the electrons in the metal foil.

26. The device of claim 1, comprising a source of the fluid to be ionised in fluid communication with the chamber.

27. The device of claim 26, including means to control passage of the fluid from the source into the chamber.

28. The device of claim 1, wherein the device quantifies ionised air in the space.

29. The device of claim 1, comprising at least one electrode and circuitry for measuring an electric current or currents generated by collision between ionised air and the at least electrode.

30. An ionisation apparatus comprising:
 a chamber configured to contain a fluid; and
 a source of soft x-rays positioned so that soft x-rays produced by the soft x-ray source pass into the chamber to ionise a fluid in the chamber;
 the soft x-ray source comprising:
  an electron source;
  circuitry for applying an electrical field to cause field emission of electrons from the electron source; and
  a target positioned for interaction with the electrons emitted from the electron source and for producing the soft x-rays in response thereto.

* * * * *